(12) United States Patent
Klinec et al.

(10) Patent No.: US 10,359,416 B2
(45) Date of Patent: Jul. 23, 2019

(54) METHOD AND DEVICE FOR ASSIGNING A BLOOD PLASMA SAMPLE

(71) Applicant: Roche Diagnostics Operations, Inc., Indianapolis, IN (US)

(72) Inventors: Darko Klinec, Calw (DE); Michael Koehler, Winnenden (DE)

(73) Assignee: Roche Diagnostics Operations, Inc.

( * ) Notice: Subject to any disclaimer, the term of this patent is extended or adjusted under 35 U.S.C. 154(b) by 0 days.

(21) Appl. No.: 15/961,266

(22) Filed: Apr. 24, 2018

(65) Prior Publication Data

US 2018/0238858 A1 Aug. 23, 2018

Related U.S. Application Data

(63) Continuation of application No. 15/234,511, filed on Aug. 11, 2016, now Pat. No. 9,983,192, which is a (Continued)

(30) Foreign Application Priority Data

Feb. 19, 2014 (EP) .................................. 14155821

(51) Int. Cl.
*G01N 33/49* (2006.01)
*G01N 21/31* (2006.01)
(52) U.S. Cl.
CPC .............. *G01N 33/49* (2013.01); *G01N 21/31* (2013.01)
(58) Field of Classification Search
CPC ........ G01N 21/31; G01N 15/14; G01N 21/47; G01N 21/6428; G01N 2333/70578; G01N 33/6803; G01N 2021/3129; G01N 21/05; G01N 21/274; G01N 21/314; G01N 2333/9108; G01N 33/49; G01N 33/492; G01N 33/5008; G01N 33/54306; G01N 33/57488; G01N 2333/4719; (Continued)

(56) References Cited

U.S. PATENT DOCUMENTS 6,064,474 A 5/2000 Lee et al.
6,353,471 B1 3/2002 Samsoondar et al.
(Continued)

FOREIGN PATENT DOCUMENTS

EP 2549264 A1 1/2013
JP S51-142392 A 7/1976
(Continued)

OTHER PUBLICATIONS

International Search Report dated Mar. 18, 2015, in Application No. PCT/EP2015/053131, 4 pages.
(Continued)

*Primary Examiner* — Michael P Stafira
(74) *Attorney, Agent, or Firm* — Roche Diagnostics Operations, Inc.

(57) ABSTRACT

A device and method for assigning a blood plasma sample to a class from a predetermined set of classes are presented. The set of classes comprises a good class, a lipemic class, a hemolytic class and an icteric class. For assignment to one of the classes, the blood plasma sample is exposed to light and measurement values dependent on transmitted or scattered light power are evaluated in order to carry out an assignment.

17 Claims, 1 Drawing Sheet

Related U.S. Application Data continuation of application No. PCT/EP2015/053131, filed on Feb. 13, 2015.

(58) Field of Classification Search
CPC ......... G01N 2333/726; G01N 2500/04; G01N 2500/20; G01N 33/5091; G01N 33/54313; G01N 33/54386; G01N 33/54393; G01N 33/566; G01N 33/56905; G01N 33/68; G01N 33/6893

See application file for complete search history.

(56) References Cited

U.S. PATENT DOCUMENTS

| | | | |
|---|---|---|---|
| 6,388,750 | B1 | 5/2002 | Liu et al. |
| 6,995,835 | B2 | 2/2006 | Samsoondar et al. |
| 2002/0167667 | A1 | 11/2002 | Samsoondar et al. |
| 2002/0176069 | A1 | 11/2002 | Hansen et al. |
| 2003/0087456 | A1 | 5/2003 | Jones et al. |
| 2005/0105077 | A1 | 5/2005 | Padmanabhan et al. |
| 2006/0014295 | A1 | 1/2006 | Ziegler |
| 2007/0002309 | A1 | 1/2007 | Yamamoto |
| 2008/0297769 | A1 | 12/2008 | Bamberg et al. |
| 2010/0248247 | A1* | 9/2010 | Kataoka ............... G01N 33/49 435/6.1 |
| 2012/0140230 | A1 | 6/2012 | Miller |
| 2012/0252127 | A1 | 10/2012 | Gregor et al. |
| 2014/0192342 | A1 | 7/2014 | Sass et al. |

FOREIGN PATENT DOCUMENTS

| | | |
|---|---|---|
| JP | S59-46539 A | 3/1984 |
| JP | 2002-040029 A | 2/2002 |
| WO | 2003/060484 A1 | 7/2003 |
| WO | 2006/011531 A1 | 2/2006 |

OTHER PUBLICATIONS

Merrick, Mark F. and Pardue, Harry L., Evaluation of Absorption and First- and Second-Derivative Spectra for Simultaneous Quantification of Bilirubin and Hemoglobin, Clinical Chemistry, 1988, pp. 598-602, vol. 32, No. 4.

* cited by examiner

METHOD AND DEVICE FOR ASSIGNING A BLOOD PLASMA SAMPLE

CROSS-REFERENCE TO RELATED APPLICATIONS

This application is a continuation of patent application Ser. No. 15/234,511, filed on Aug. 11, 2016, now allowed, which is a continuation of PCT/EP2015/053131, filed Feb. 13, 2015, which is based on and claims priority to EP 14155821.3, filed Feb. 19, 2014, which are hereby incorporated by reference.

BACKGROUND

The present disclosure relates to a method and a device for assigning a blood plasma sample to a class from a predetermined set of classes, where the blood plasma sample is contained in an at least partially transparent vessel.

Blood samples are often used in order to be able to diagnose particular illnesses or, alternatively, in order to be able to detect criminal offences or infringements of regulations such as, for example, the consumption of drugs or driving under the influence of alcohol. Such a blood sample is typically introduced into a light-transparent vessel in the form of a plastic tube, such a tube being configured in a similar way to a test tube. In the tube, the sample is typically centrifuged before further analysis steps, so that a blood precipitate, in which all the cellular constituents of the blood sample are concentrated, is formed at the lower end of the tube. Above the blood precipitate, there is then typically blood plasma which essentially contains the liquid constituents of the blood sample. The blood plasma, which forms a blood plasma sample, is generally analyzed in subsequent analysis steps.

Often, before further analysis steps, it is expedient to carry out at least a rough determination of whether the blood plasma sample indicates a particular pathological state, or has particular features in another way. To this end, the blood plasma sample may be assigned to a class from a predetermined set of classes, such assignment generally being carried out manually. This is in particular because blood plasma samples are usually provided with extensive labels which indicate data such as the name of the patient or the date of the sampling. However, such labels prevent the transparency of the vessel from being utilized in order to carry out preliminary analysis of the blood plasma sample by optical methods.

Typical classes assigned to a blood plasma sample at the stage relevant here are, for example, a lipemic class, a hemolytic class, an icteric class and a good class. The "good" class contains those samples which are not assigned to the class lipemic, hemolytic or icteric.

When the sample is to be assigned to the lipemic class, it is a lipemic sample which has an elevated level of lipids. This may, for example, be an indication of a disorder of the fat metabolism.

When the sample is to be assigned to the hemolytic class, it is a hemolytic sample which has an elevated level of hemoglobin. This may, for example, be an indication of particular anemias, transfusion reactions or malaria.

When the blood plasma sample is to be assigned to the icteric class, it is an icteric sample which has an elevated level of bilirubin. This may, for example, be an indication of a disease of the liver.

There is a need for a device and method for assigning a blood plasma sample to a class of predetermined set of classes that allows automated assignment even in the case of labeled vessels.

SUMMARY

According to the present disclosure, a device and method for assigning a blood plasma sample to a class from a predetermined set of classes are presented. The blood plasma sample can be contained in an at least partially transparent vessel. The method can comprise exposing the blood plasma sample to light. The spectral composition of the light can comprise at least wavelengths from a predetermined set of wavelengths. The method can further comprise forming a wavelength-specific measurement value for a respective wavelength from the set of wavelengths. A respective measurement value can be dependent on a light power transmitted through the blood plasma sample and the vessel at the respective wavelength. The method can further comprise assigning the blood plasma sample to a class as a function of the wavelength-specific measurement values. The predetermined set of classes can comprise a hemolytic class. The set of wavelengths can comprise a first hemolytic wavelength in the range of from 535 nm to 547 nm and a second hemolytic wavelength in the range of from 510 nm to 520 nm and the blood plasma sample can be assigned to the hemolytic class if a ratio of the measurement value at the first hemolytic wavelength and the measurement value at the second hemolytic wavelength is less than a first relative hemolytic threshold value.

Accordingly, it is a feature of the embodiments of the present disclosure to provide a device and method for assigning a blood plasma sample to a class of predetermined set of classes that allows automated assignment even in the case of labeled vessels. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
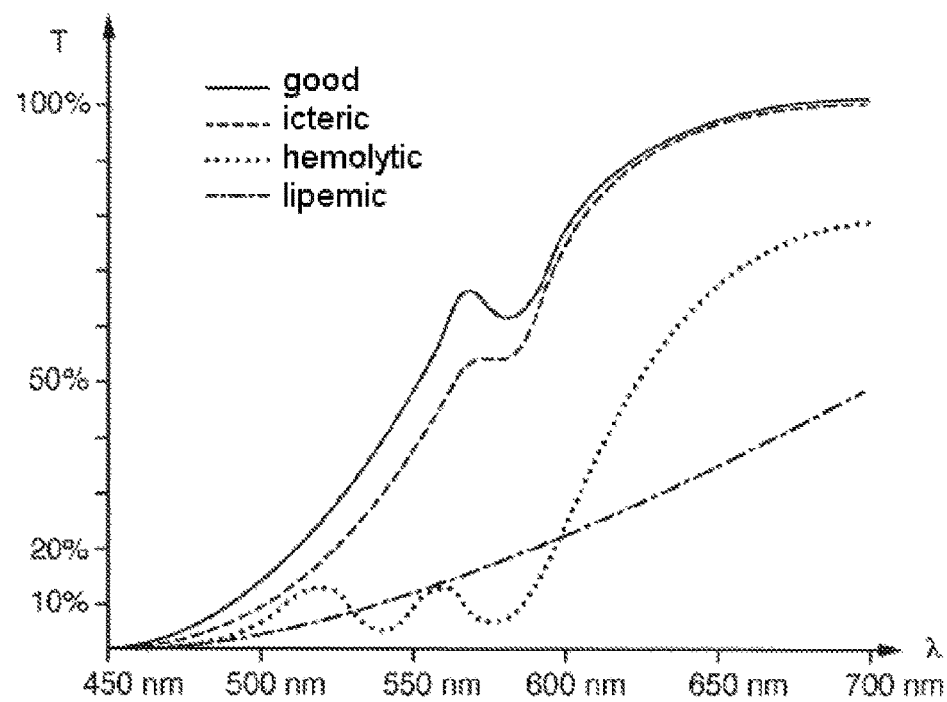
FIG. 1 illustrates typical transmission spectra in the visible wavelength range for different classes of samples according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for assigning a (e.g., blood plasma) sample to a class from a predetermined set of classes is presented. The blood plasma sample, optionally together with other layerwise arranged constituents such as blood precipitate, separating gel, and the like can be contained in an, at least, partially transparent vessel. The method can comprises exposing the blood plasma sample to light, the spectral composition of which can comprise at least wavelengths from a set of different wavelengths, forming a wavelength-dependent measurement value for a respective wavelength from the set of wavelengths, a respective measurement value can be dependent on a light power, transmitted through the blood plasma sample and the vessel, or transmitted light intensity at the respective wavelength, and assigning the blood plasma sample to a class as a function of the wavelength-specific measurement values.

The predetermined set of classes can comprise a hemolytic class. The set of wavelengths can comprise a first hemolytic wavelength in the range from about 535 nm to about 547 nm. In one embodiment, the first hemolytic wavelength can be 541 nm. The set of wavelengths can also comprise a second hemolytic wavelength in the range from about 510 nm to about 520 nm. In one embodiment, the second hemolytic wavelength can be 515 nm. The blood plasma sample can be assigned to the hemolytic class when a ratio of the measurement value at the first hemolytic wavelength and the measurement value at the second hemolytic wavelength is less than a first relative hemolytic threshold value.

This procedure can be based on the transmission at a wavelength of about 515 nm being influenced only little by hemoglobin. The measurement value at this wavelength can therefore be used as a reference for the measurement value at a wavelength of about 541 nm. In contrast to determination by comparison of the absolute value of the measurement value with an absolute hemolytic threshold value, in the comparison just described of a ratio, i.e. a relative value, with the relative hemolytic threshold value, it may not be necessary to rule out it being a lipemic sample, in order to be able to determine reliably a hemolytic sample. This can be because a particularly low ratio of the measurement value at the first hemolytic wavelength and the measurement value at the second hemolytic wavelength can occur only in hemolytic samples.

The ratio of the measurement value at the first hemolytic wavelength and the measurement value at the second hemolytic wavelength may be calculated as follows:
ti $V=M1/M2$,
where V denotes the ratio of the measurement values, M1 denotes the measurement value at the first hemolytic wavelength and M2 denotes the measurement value at the second hemolytic wavelength. M2 is consequently used as a reference (value).

The following applies for the assignment to the hemolytic class:

$V<S$ where S denotes the first relative hemolytic threshold value.

The first relative hemolytic threshold value S may be less than about 1. In another embodiment the first relative hemolytic threshold value S can be less than 0.75. In yet another embodiment, the first relative hemolytic threshold value S can be less than 0.5.

Contrary to the prior art, the present disclosure is based on it being possible to carry out assignment of the blood plasma sample by transmitted light even if there is a label on the vessel. By this method, reliable and rapid automatic testing of blood plasma samples can be possible, which can make it possible to use the method in an analysis system configured for high throughput.

During the formation of a wavelength-specific measurement value, either precisely one wavelength-specific measurement value may be formed or a plurality of wavelength-specific measurement values at the same wavelength may be formed, an average value of the measurement values being, for example, formed.

The respective measurement value may be dependent on a light power transmitted in a straight line through the blood plasma sample and the vessel. In this case, determination is carried out of which fraction of the light emitted on one side passes in a straight line through the sample and which fraction is absorbed inside the sample, or else scattered. This information may be used in order to assign the blood plasma sample to a class.

According to one embodiment, the predetermined set of classes can comprise a lipemic class. The set of wavelengths can comprise a lipemic wavelength in the range from about 610 nm to about 700 nm. In one embodiment, the lipemic wavelength can be 650 nm or 685 nm. The blood plasma sample can be assigned to the lipemic class when the measurement value at the lipemic wavelength is less than a lipemic threshold value.

This embodiment can be based on the fact that lipids can reduce the transmission through the blood plasma sample particularly in the range from about 610 nm to about 700 nm and especially at 650 nm and at 685 nm. Therefore, a lipemic sample can be detected by comparing the corresponding measurement value with a suitably selected lipemic threshold value.

According to one embodiment, the predetermined set of classes can comprise a lipemic class. A scattering measurement value can be formed, which can be dependent on a light power, scattered by the blood plasma sample, or scattered light intensity, the blood plasma sample being assigned to the lipemic class when the scattering measurement value is greater than a lipemic scattering threshold value. This scattering measurement may be combined with the transmission measurement. The scattering measurement value may be dependent on a light power scattered laterally, for example, at an angle of about 90° relative to transmission in a straight line. This may, for example, be achieved by arranging a corresponding detector.

The scattering measurement value may be dependent on an elastically scattered light power or on an elastically scattered light intensity. In this context, elastically means that the lipemic wavelength remains constant throughout the scattering process.

The detection of a lipemic sample with the aid of such a scattering measurement value is based on the discovery that lipids scatter certain wavelengths particularly strongly. This does not apply for any of the other substances relevant here to be determined in the blood plasma sample. The use of a scattering measurement value can therefore be suitable for the detection of a lipemic sample.

According to one embodiment, the blood plasma sample can be assigned to the hemolytic class when the measurement value at the first hemolytic wavelength is less than an absolute hemolytic threshold value and when the blood plasma sample is not assigned to a lipemic class.

This embodiment is based on the transmission in the case of a sample containing hemoglobin being low at a wavelength of about 541 nm, which may in principle be used for the detection of a hemolytic sample. In the case of a high lipid content, however, a lipemic sample likewise can have only a low transmission at the aforementioned wavelength. Only considering the measurement value at a wavelength of about 541 nm can therefore not be sufficient in order to detect a hemolytic sample reliably. The blood plasma sample can therefore be assigned to the hemolytic class on the basis of a comparison of the absolute value of the measurement value with the absolute hemolytic threshold value only if it can be ensured that it is not a lipemic sample. Since, as described above, a lipemic sample can be detected reliably at much longer wavelengths or by scattered light, in this way it can be possible to distinguish hemolytic, lipemic and good samples from one another reliably. It can be mentioned that the establishment that it is not a lipemic sample need not necessarily be based on the disclosed method and not necessarily on an optical measurement. It may, for example, also be ensured by external factors that lipemic samples do not reach the point at which the method is carried out, for example by an upstream sorting device or because samples come only from a particular hospital department.

According to one embodiment, the set of wavelengths can comprise a third hemolytic wavelength in the range of about 610 nm to about 700 nm. In one embodiment, the third hemolytic wavelength can be 650 nm or 685 nm. The blood plasma sample can be assigned to the hemolytic class when a ratio of the measurement value at the first hemolytic wavelength and the measurement value at the third hemolytic wavelength is less than a second relative hemolytic threshold value.

This embodiment is based on the fact that a measurement value at a wavelength from about 610 nm to about 700 nm may also be used as a reference value instead of the above-described wavelength of about 515 nm. A particularly low value of the described ratio of the measurement value at the first hemolytic wavelength and the measurement value at the third hemolytic wavelength can occur only in the case of a hemolytic sample so that this ratio may also be used reliably on its own for the detection of a hemolytic sample. It can be mentioned that the measurement value at the third hemolytic wavelength can be particularly low in the case of a lipemic sample so that the ratio described here can increase.

The ratio of the measurement value at the first hemolytic wavelength and the measurement value at the third hemolytic wavelength may be calculated as follows:

$$V2 = M1/M3,$$

where V2 denotes the ratio of the measurement values, M1 denotes the measurement value at the first hemolytic wavelength and M3 denotes the measurement value at the third hemolytic wavelength. M3 is consequently used as a reference (value).

The following applies for the assignment to the hemolytic class:

$$V2 < S2$$

where S2 denotes the second relative hemolytic threshold value.

The second relative hemolytic threshold value S2 may be less than about 1. In another embodiment, the second relative hemolytic threshold value S2 may be less than 0.25. In yet another embodiment, the second relative hemolytic threshold value S2 may be less than 0.1.

According to one embodiment, the predetermined set of classes can comprise an icteric class. The set of wavelengths can comprise a first icteric wavelength in the range from about 450 nm to about 485 nm. In one embodiment, the first icteric wavelength can be 470 nm. The blood plasma sample can be assigned to the icteric class when the measurement value at the first icteric wavelength is less than an absolute icteric threshold value and when the blood plasma sample is not assigned to a lipemic class and is not assigned to a hemolytic class.

This procedure can be based on the fact that a particularly low transmission in the range from about 450 nm to about 485 nm such as, for example, at about 470 nm, can occur in icteric samples because of the bilirubin contained. A low transmission in this wavelength range may however also occur in lipemic samples or in hemolytic samples, especially in the case of a particularly high concentration of lipids or hemoglobin. It can therefore be preferable to assign a blood plasma sample to the icteric class on the basis of a comparison of the absolute value of the measurement value at the first icteric wavelength with the absolute icteric threshold value only if it can be ruled out that it is a lipemic sample or a hemolytic sample. This may, as described above, be done outside the range from about 450 nm to about 485 nm. In this way, icteric, hemolytic, lipemic and good samples can be distinguished reliably from one another.

In this case as well, it can be possible to rule out by external measures, as described above, that it is a lipemic sample or a hemolytic sample.

According to one embodiment, the predetermined set of classes can comprise an icteric class. The set of wavelengths can comprise a first icteric wavelength in the range from about 450 nm to about 485 nm such as, for example, 470 nm and a second icteric wavelength in the range from about 510 nm to about 520 nm such as, for example, 515 nm. The blood plasma sample can be assigned to the icteric class when a ratio of the measurement value at the first icteric wavelength and the measurement value at the second icteric wavelength is less than a first relative icteric threshold value. The first relative icteric threshold value may, for example, be about 0.1.

This procedure can be based on the fact that the transmission through a blood plasma sample in the range from about 510 nm to about 520 nm such as, for example at 515 nm, may be used as a reference for the determination of an icteric sample, in the same way as was already explained above with reference to a hemolytic sample. A separate safeguard that it is not a hemolytic or lipemic sample may be omitted, because a particularly low ratio of the measurement value at the first icteric wavelength and the measurement value at the second icteric wavelength can occurs only in the case of an icteric sample.

The second icteric wavelength may be equal to the second hemolytic wavelength. This can be favorable when the predetermined set of classes comprises both an icteric class and a hemolytic class, since one wavelength may then be used for the assignment to both classes. Outlay on apparatus can thereby be reduced.

According to one embodiment, the predetermined set of classes can comprise an icteric class. The set of wavelengths can comprise a first icteric wavelength in the range from about 450 nm to about 485 nm such as, for example, 470 nm, and a third icteric wavelength in the range from about 610 nm to about 700 nm such as, for example, 650 nm or 685 nm. The blood plasma sample can be assigned to the icteric class when a ratio of the measurement value at the first icteric wavelength and the measurement value at the third icteric wavelength is less than a second relative icteric threshold value. The second relative icteric threshold value may, for example, be about 0.1.

This procedure can be based on the fact that the wavelength range from about 610 nm to about 700 nm, and in particular 650 nm or 685 nm, may likewise be used as a reference for the determination of an icteric sample like the above-described wavelength range from about 510 nm to about 520 nm. This can rely on the fact that the measurement value in this wavelength range is not reduced, or is reduced only little, in an icteric sample.

The third icteric wavelength may be equal to the third hemolytic wavelength. This can be favorable in particular when the set of classes comprises both an icteric class and a hemolytic class. As already described above, outlay on apparatus can be reduced by such a procedure.

According to one embodiment, the predetermined set of classes can comprise a good class. The blood plasma sample can be assigned to the good class when the blood plasma sample is not assigned to a lipemic class, is not assigned to a hemolytic class and is not assigned to an icteric class.

The described procedure may mean that, for a sample, a check can be made as to whether it is a lipemic sample, whether it is a hemolytic sample and whether it is an icteric sample. Only when it is established that it is not a lipemic sample, not a hemolytic sample, and not an icteric sample, can the blood plasma sample be assigned to the good class. It may, however, also mean that one or two of the described classes are not checked, and therefore the blood plasma sample can already be assigned to the good class when it is established that it is not one of the checked classes of samples. This may for example be favorable when, due to influencing factors which lie outside a testing system used for carrying out the method, i.e. by external measures, it can be ensured or at least unlikely that a particular class of samples occurs, or even that two particular classes of samples occur.

According to one embodiment, an error message can be emitted when the blood plasma sample is assigned to at least two different classes. An error message may, for example, be an acoustic warning sound and/or an error indication on a display. This can accommodate the fact that for this case it is likely that at least one detection method for a particular class of samples has failed and manual determination of the class of the blood plasma sample or termination of further analysis steps may be advisable.

According to one embodiment, the method can comprise detecting whether, and also at what position, there is a label on the vessel, a number of threshold values being modified as a function thereof. Under certain circumstances, rotation of the sample may also be carried out in such a way that the transmitted light needs to pass through as few label layers as possible.

This can accommodate the fact that the transmission at all wavelengths can be modified when a light beam used for the measurement passes through this label. In this case, it can also be possible to distinguish whether the light beam passes through the label only on entry or on exit, or both on entry and on exit. By the adaptation of threshold values as a function of such detection, the reliability of the method which carries out an assignment of the sample to a class on the basis of the comparison with such a threshold value can be increased.

In principle, all threshold values used may be modified. It can also be possible to modify a subgroup of the threshold values used. In particular, the threshold values described above may be modified.

It may be expedient to modify the absolute threshold values, since in the case of a comparison of absolute values there is no correction by a reference value which would likewise be subject to the influence of the label. One threshold value or a plurality of threshold values, from the group of threshold values which can comprise of the absolute lipemic threshold value, the lipemic scattering threshold value, the absolute hemolytic threshold value and the absolute icteric threshold value, may therefore be modified. Likewise, however, the relative threshold values may also be modified, i.e. for example one threshold value or a plurality of threshold values from the group of threshold values which can comprise of the first relative hemolytic threshold value, the second relative hemolytic threshold value, the first relative icteric threshold value and the second relative icteric threshold value.

According to one refinement, it can also be possible to detect whether the light beam passes through a plurality of labels, i.e. not just through one label. The aforementioned threshold values may also be modified in a suitable way as a function thereof.

The described modification of threshold values can be especially advantageous when a comparatively low light power is used. In the case of high light powers, the influence of labels may also be sufficiently low, so that the modification of threshold values may be omitted.

The step of detecting whether, and also at what position, there is a label on the vessel can be carried out by a camera. It can however also be possible to use other measuring instruments such as, for example a photodetector.

A device for assigning a blood plasma sample contained in an at least partially transparent vessel, by using the aforementioned method is also presented. The device can comprise a light source which can emit light, the spectral composition which can comprise at least one wavelength from the predetermined set of wavelengths according to the method, onto the vessel, a detector arrangement, which can receives light transmitted (in a straight line) through the blood plasma sample and the vessel and can determine therein a measurement value dependent on the transmitted light power or the transmitted light intensity for each of the wavelengths from the set of wavelengths, and a control device, which can be connected to the detector arrangement in order to record the measured measurement values and can be configured to carry out the disclosed method. The control device may, for example, be a conventional personal computer on which a program on which the disclosed method is run.

The method can be carried out using such a device. The device therefore can make it possible to detect the class of a blood plasma sample, or in other words, to assign a blood plasma sample to a class, without manual intervention being necessary therefor, even if there is a label on the vessel.

When carrying out the disclosed method with the disclosed device, all above-described configurations of the method may be employed in any desired combination. The advantages explained apply accordingly.

According to one embodiment, the detector arrangement can comprise, for each wavelength from the set of wavelengths, a detector, a filter arranged upstream of the detector, and a light-guiding fiber for receiving light transmitted through the sample and the vessel.

A detector may, for example, be a conventional photodetector such as, for example, a semiconductor detector.

The filter may, for example, be an optical filter or an interference filter. Such a filter conventionally can have only a narrow transmission range, so that a wavelength range of only one or only a few nanometers can be transmitted in a narrowband through the filter. Such filters may also be referred to as bandpass filters. It can therefore be possible to determine the wavelength, or the wavelength range, from which the downstream detector records a measurement value.

The use of light-guiding fibers can allow reliable light guiding to a position at which a detector is located, which can increase the freedom in arranging the detectors. Furthermore, it can therefore readily be possible to use a plurality of detectors, which can be problematic if it is necessary to fit detectors directly on the vessel.

The device may comprise a further detector arrangement, which can receive light scattered laterally such as, for example, with an angle of about 90°, by the blood plasma sample relative to propagation in a straight line, and can determine a further measurement value dependent on the scattered light power or the scattered light intensity, the control device being connected to the further detector arrangement in order to record the further measurement value.

It can therefore be possible to carry out a method based on the measurement of scattered light, as was explained above with reference to the assignment of a blood plasma sample to the lipemic class.

The control device may, for example, be a conventional computer or another electronic device having a processor, a storage medium and suitable interfaces.

The device may comprise a camera with which labels on the vessel can be detected. To this end, suitable known image recognition algorithms may be used. This can be suitable for the above-described variation of threshold values as a function of whether a light beam passes through a label or through a plurality of labels.

Referring initially to FIG. 1, FIG. 1 shows a typical, schematically represented transmission spectra of good, icteric, hemolytic and lipemic samples. The wavelength (λ) in the range from about 450 nm to about 700 nm, i.e. approximately in the visible spectrum, can be represented in this case on the horizontal axis. The transmission (T) in values from about 0% to about 100% can be represented on the vertical axis.

The solid curve shows a typical transmission spectrum of a good sample. It can be seen that the value of the transmission rises from about 0% to 100% over the wavelength range shown from about 450 nm to about 700 nm. Between about 550 nm and about 600 nm, the curve can be structured, specifically with a maximum and a minimum.

The dashed curve shows a typical transmission spectrum of an icteric sample. It can be seen that, in the range below about 600 nm, the transmission lies below that of a good sample. This may be used in order to detect an icteric sample. In particular, the value of the transmission at a wavelength of about 470 nm is less than in the case of a good sample.

The dotted curve shows a typical transmission spectrum of a hemolytic sample. It can be seen that the transmission in such a hemolytic sample essentially lies below the transmission of a good sample. Furthermore, such a hemolytic sample can have an additional minimum in the transmission curve at a wavelength of about 541 nm (as well as at about 580 nm). This may be used in order to detect such a hemolytic sample.

The curve represented in dots and dashes shows a typical transmission spectrum of a lipemic sample. It can be seen that the transmission in such a lipemic sample lies essentially below the transmission of a good sample. In particular, this applies to the range from about 610 nm to about 700 nm, which may be used in order to detect such a lipemic sample.

Figure 2:
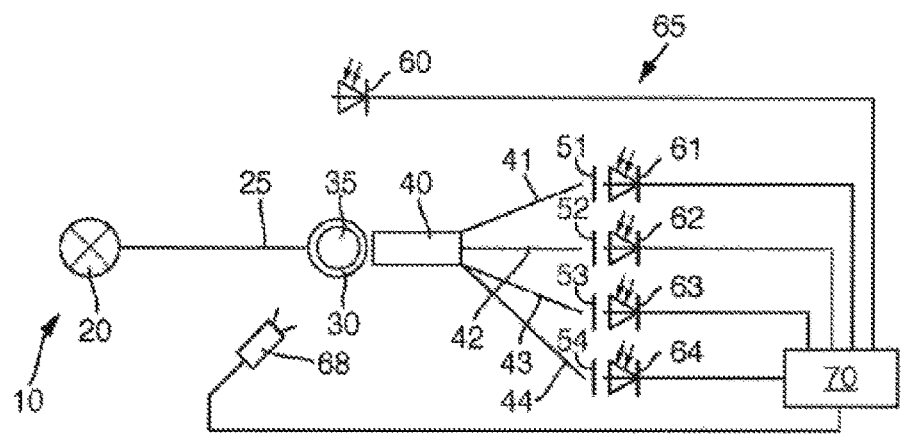
FIG. 2 illustrates a device for assigning a blood plasma sample, which carries out a method for assigning a blood plasma sample to a class according to an embodiment of the present disclosure.

FIG. 2 shows a device 10 for assigning a blood plasma sample to a class from a predetermined set of classes. The device 10 can comprise a light source in the form of a halogen lamp 20, which can emit a light beam 25 with a broadband spectrum. The term light beam can also include split beams.

The device 10 can comprise a sample holder 30, in which an at least partially transparent vessel 35 can be received. In the vessel 35, there can be a centrifuged blood sample, or blood plasma sample.

The light beam 25 can strike the vessel 35 and can pass through the vessel 35. The vessel 35 can be oriented with respect to the light source 20 in such a way that the light beam 25 can pass through the blood plasma.

Provided opposite the halogen lamp 20, next to the sample holder 30, there can be a light collector 40 which can receive that part of the light beam 25 that is transmitted through the vessel 35, and therefore also through the sample. Light-guiding fibers in the form of a first glass fiber cable 41, a second glass fiber cable 42, a third glass fiber cable 43 and a fourth glass fiber cable 44 can extend from the light collector 40.

The first glass fiber cable 41 can lead to a first bandpass filter 51, behind which there can be a first photodiode 61. The second glass fiber cable 42 can lead to a second bandpass filter 52, behind which there can be a second photodiode 62. The third glass fiber cable 43 can lead to a third bandpass filter 53, behind which there can be a third photodiode 63. The fourth glass fiber cable 44 can lead to a fourth bandpass filter 54, behind which there can be a fourth photodiode 64.

In addition, a further photodiode 60, which can detect scattered light, can be arranged laterally with respect to the path of the light beam 25. Together, the light collector 40, the glass fiber cables 41, 42, 43, 44, the bandpass filters 51, 52, 53, 54, the further photodiode 60 and the first, second, third and fourth photodiodes 61, 62, 63, 64 can form a detector arrangement 65. It can be understood that further glass fiber cables and associated photodiodes may be provided for corresponding further wavelengths.

The device 10 can furthermore comprise a camera 68 to record the vessel 35 in the sample holder 30. In this way, for example, a label and a position of the label on the vessel 35 can be detected.

The photodiodes 60, 61, 62, 63, 64 and the camera 68 can be connected to an electronic control device 70. The latter can record signals of the photodiodes 60, 61, 62, 63, 64 and of the camera 68, in order to assign the sample contained in the vessel 35 to a class from a set of predetermined classes by the disclosed method. These classes can be a lipemic class, a hemolytic class, an icteric class and a good class.

The first bandpass filter 51 can have a transmission maximum at 685 nm corresponding to a lipemic wavelength. If a measurement value determined by the first photodiode 61 is less than a predetermined lipemic threshold value, the electronic control device 70 can assign the sample to the lipemic class. Furthermore, the sample can likewise be assigned to the lipemic class when a measurement value of the further photodiode 60 detecting scattered light is greater than a lipemic scattering threshold value. If the two described possibilities for assigning the sample to the lipemic class lead to different results, an error message can be emitted.

The second bandpass filter 52 can have a transmission maximum at 541 nm corresponding to a first hemolytic wavelength. If a measurement value detected by the second photodiode 62 is less than a predetermined absolute hemolytic threshold value, and if at the same time the sample has not been assigned to the lipemic class, the electronic control device 70 can assign the sample to the hemolytic class. Furthermore, the electronic control device 70 can also calculate a ratio of the measurement values measured by the second detector 62 and the first detector 61. If this ratio is less than a relative hemolytic threshold value, the electronic control device 70 can likewise assign the sample to the hemolytic class. If the two described possibilities for assigning the sample to the hemolytic class lead to different results, an error message can be emitted.

The third bandpass filter 53 can have a transmission maximum at 515 nm corresponding to a second icteric wavelength. The fourth bandpass filter 54 can have a transmission maximum at 470 nm corresponding to a first icteric wavelength. If a measurement value measured by the fourth photodiode 64 is less than an absolute icteric threshold value, and if at the same time the blood plasma sample is assigned neither to the lipemic class nor to the hemolytic class, the electronic control device 70 can assign the sample to the icteric class. Furthermore, the electronic control device 70 can also calculate a ratio of the measurement values measured by the fourth detector 64 and the third detector 63. If this ratio is less than a relative icteric threshold value, the electronic control device 70 can likewise assign the sample to the icteric class. If the two described possibilities for assigning the sample to the icteric class lead to different results, an error message can be emitted.

If the control device 70 does not assign the sample to the lipemic class, to the hemolytic class or to the icteric class, it can assign the sample to the good class.

By an image delivered by the camera 68, the electronic control device 70 can determine whether the light beam 25 can travel unimpeded on its path through the vessel 35 and the sample contained therein, or the blood plasma contained therein, or whether it has to pass through one or more labels. Unimpeded travel can be intended to mean that the light beam 25 passes only through the sample, or the blood plasma contained therein, and through transparent parts of the vessel 35. As a function thereof, the electronic control device 70 can modify the aforementioned threshold values in a predetermined way. In particular, when it has been discovered that the light beam 25 has to pass through at least one label, the absolute threshold values can be reduced since in this case, the light beam is partially absorbed by the label.

By the assignment of the sample to a class, carried out in the control device 70, subsequent analysis steps may be simplified or planned better. If an error message is emitted, manual intervention may be initiated in order to prevent incorrect analyses.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A device for assigning a blood plasma sample to a class from a predetermined set of classes, the blood plasma sample being contained in an at least partially transparent vessel, the device comprising:
    a light source configured to emit light, the spectral composition of which comprises at least wavelengths from a predetermined set of wavelengths, onto the vessel;
    a detector arrangement configured to receive light transmitted through the blood plasma sample and the vessel and to measure therein a measurement value dependent on the transmitted light power for each of the wavelengths from the set of wavelengths; and
    a control device connected to the detector arrangement in order to record the measurement values and configured to assign the blood plasma sample to a class as a function of the recorded measurement values, wherein the predetermined set of classes comprises a hemolytic class, wherein the set of wavelengths comprises a first hemolytic wavelength in the range of from 535 nm to 547 nm and a second hemolytic wavelength in the range of from 510 nm to 520 nm, and wherein the blood plasma sample is assigned to the hemolytic class if a ratio of the measurement value at the first hemolytic wavelength and the measurement value at the second hemolytic wavelength is less than a first relative hemolytic threshold value.

2. The device according to claim 1, wherein the detector arrangement comprises, for each wavelength from the set of wavelengths, a detector, a filter arranged upstream of the detector, and a light-guiding fiber for receiving light transmitted through the sample and the vessel.

3. The device according to claim 1, further comprising,
    a further detector configured to receive light scattered laterally by the blood plasma sample relative to propagation in a straight line and to measure a measurement value dependent on the scattered light power, wherein the control device is connected to the further detector in order to record the measured measurement value.

4. The device according to claim 3, wherein the further detector receives light scattered laterally at an angle of 90° relative to transmission in a straight line.

5. The device according to claim 1, wherein the first hemolytic wavelength is 541 nm.

6. The device according to claim 1, wherein the second hemolytic wavelength is 515 nm.

7. The device according to claim 1, wherein the predetermined set of classes comprises a lipemic class, the set of wavelengths comprises a lipemic wavelength in the range of from 610 nm to 700 nm, and the blood plasma sample is assigned to the lipemic class if the measurement value at the lipemic wavelength is less than a lipemic threshold value.

8. The device according to claim 7, wherein the lipemic wavelength is 650 nm or 685 nm.

9. The device according to claim 3, wherein the predetermined set of classes comprises a lipemic class and a scattering measurement value is formed dependent on a light power scattered by the blood plasma sample, wherein the blood plasma sample is assigned to the lipemic class if the scattering measurement value is greater than a lipemic scattering threshold value.

10. The device according to claim 1, wherein the blood plasma sample is assigned to the hemolytic class if the measurement value at the first hemolytic wavelength is less than an absolute hemolytic threshold value and if the blood plasma sample is not assigned to a lipemic class.

11. The device according to claim 1, wherein the set of wavelengths comprises a third hemolytic wavelength in the range of from 610 nm to 700 nm and the blood plasma sample is assigned to the hemolytic class if a ratio of the measurement value at the first hemolytic wavelength and the measurement value at the third hemolytic wavelength is less than a second relative hemolytic threshold value.

12. The device according to claim 11, wherein the third hemolytic wavelength is 650 nm or 685 nm.

13. The device according to claim 1, wherein the predetermined set of classes comprises an icteric class, the set of wavelengths comprises a first icteric wavelength in the range of from 450 nm to 485 nm, and the blood plasma sample is assigned to the icteric class if the measurement value at the first icteric wavelength is less than an absolute icteric threshold value and if the blood plasma sample is not assigned to a lipemic class and is not assigned to a hemolytic class.

14. The device according to claim 13, wherein the first icteric wavelength is 470 nm.

15. The device according to claim 1, wherein the predetermined set of classes comprises an icteric class, the set of wavelengths comprises a first icteric wavelength in the range of from 450 nm to 485 nm and a second icteric wavelength in the range of from 510 nm to 520 nm, and the blood plasma sample is assigned to the icteric class if a ratio of the measurement value at the first icteric wavelength and the measurement value at the second icteric wavelength is less than a first relative icteric threshold value.

16. The device according to claim 15, wherein the second icteric wavelength is 515 nm.

17. The device according to claim 1, wherein the predetermined set of classes comprises a good class, and the blood plasma sample is assigned to the good class if the blood plasma sample is not assigned to a lipemic class, is not assigned to a hemolytic class and is not assigned to an icteric class.

* * * * *